United States Patent
Yao et al.

(10) Patent No.: US 7,807,737 B2
(45) Date of Patent: *Oct. 5, 2010

(54) PHOSPHORUS-CONTAINING FLAME RETARDANT FOR THERMOPLASTIC POLYMERS

(75) Inventors: Qiang Yao, Yorktown Heights, NY (US); Sergei V. Levchik, Croton-on-Hudson, NY (US); Gerald R. Alessio, Emerson, NJ (US)

(73) Assignee: ICL-IP America Inc., Ardsley, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/630,721

(22) PCT Filed: Jun. 20, 2005

(86) PCT No.: PCT/US2005/021726

§ 371 (c)(1),
(2), (4) Date: Aug. 29, 2007

(87) PCT Pub. No.: WO2006/009983

PCT Pub. Date: Jan. 26, 2006

(65) Prior Publication Data

US 2008/0132619 A1    Jun. 5, 2008

Related U.S. Application Data

(60) Provisional application No. 60/581,832, filed on Jun. 22, 2004.

(51) Int. Cl.
  *C08K 5/49* (2006.01)
(52) U.S. Cl. .......................... 524/115; 556/174; 562/8; 524/113
(58) Field of Classification Search ................. 524/126, 524/115
  See application file for complete search history.

(56) References Cited

U.S. PATENT DOCUMENTS

| | | | | |
|---|---|---|---|---|
| 3,962,172 A | * | 6/1976 | Wurmb et al. | 523/209 |
| 4,208,321 A | | 6/1980 | Sandler | |
| 5,773,556 A | * | 6/1998 | Kleiner et al. | 528/321 |
| 5,869,722 A | * | 2/1999 | Kleiner | 556/174 |
| 6,211,402 B1 | * | 4/2001 | Kleiner | 562/8 |
| 6,355,832 B1 | | 3/2002 | Weferling et al. | |

FOREIGN PATENT DOCUMENTS

| | | | |
|---|---|---|---|
| EP | 0 794 220 | * | 2/1997 |
| EP | 0794220 | | 9/1997 |
| EP | 1500676 | | 1/2005 |
| WO | 2005/331192 | | 4/2005 |

* cited by examiner

*Primary Examiner*—Vasu Jagannathan
*Assistant Examiner*—Doris L Lee
(74) *Attorney, Agent, or Firm*—Dilworth & Barrese, LLP

(57) ABSTRACT

A flame retarded thermoplastic polymer composition comprising a thermoplastic polymer and a metal salt of phosphinic acid possessing a desired degree of volatility.

13 Claims, 1 Drawing Sheet

PHOSPHORUS-CONTAINING FLAME RETARDANT FOR THERMOPLASTIC POLYMERS

CROSS-REFERENCE TO RELATED APPLICATIONS

This application claims the benefit of Provisional U.S. Patent Application Ser. No. 60/581,832 filed Jun. 22, 2004, the entire contents of which are incorporated by reference herein.

FIELD OF THE INVENTION

This invention relates to a highly efficient phosphorus-containing flame retardant and its use in thermoplastic polymers, more particularly, in polyester and nylon materials.

BACKGROUND OF THE INVENTION

The flame retardant performance of polyesters or nylons can be achieved by the incorporation of various types of additives. Typically, halogenated compounds, more specifically, aromatic polybrominated compounds, have been used as flame retardant additives in such polymers. It is generally accepted that these products inhibit radical gas phase reactions from occurring in the flame when these products are ignited. This makes halogenated flame retardants very commonly used additives for different types of polymeric materials including polyesters and nylons. However, during the last fifteen years or so, halogenated flame retardants have come under scrutiny because of ecological concerns. At this time, the flame retardant industry is under pressure to change to flame retardant additives that are perceived to be more environmentally friendly.

Phosphorus-containing products are logical substitutes for such halogenated flame retardants. In some applications, phosphorus-containing additives show as high an activity as the halogenated ones, but the phosphorus-containing additives are less commonly employed. Most of the phosphorus-containing flame retardants provide flame retardant activity through a combination of condensed phase reactions, polymer carbonization promotion, and char formation. These processes obviously depend on the polymer in which such additive(s) are employed. Therefore, specific phosphorus-containing structures need to be designed for various polymers types. Phosphorus-containing flame retardants also provide flame retardant activity through a gas-phase mechanism. However, because phosphorus-containing compounds tend to react with the decomposing polymer in the course of combustion instead of merely being volatilized, high gas-phase activity of phosphorus additives is relatively rare.

In late 1970s and early 1980s various salts, such as zirconium or zinc salts, of diarylphosphinates, alkyl-arylphosphinates or dialkylphosphinates were prepared, as illustrated, for example, by U.S. Pat. Nos. 4,180,495; 4,208,321; and 4,208,322. These phosphinate salts were added to PET or copolymerized with the polyester. At levels of 10-20 wt. %, an improvement of flammability retardation, as measured by the oxygen index (OI) of from 1 to 4 units, was observed.

Later on, a variety of alkylphosphinic acid metal salts of zinc (M=Zn) or aluminum (M=Al), as described by formulae I to IV shown below, were tested in PBT (see European Patent Publication No. 794,220). It was found that the aluminum salt of ethylmethylphosphinic acid (I) gave a V-0 rating in the UL-94 test at 15 wt. % loading in plain PBT and at 20 wt. % loading in glass-filled PBT. The calcium salts of dialkylphos-phinic acids (M=Ca) were proven to be as efficient as the aluminum salts and provided a V-0 rating in glass-filled PBT at 20 wt. % loading (see U.S. Pat. No. 5,780,534 and European Patent Publication No. 941,996). These phosphinic acid salts are not particularly efficient in glass-filled nylons and provide a V-0 rating only at 30 wt. % loading.

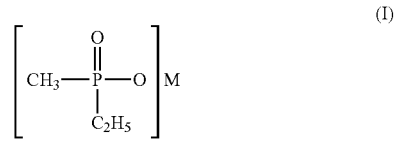

(I)

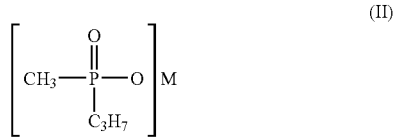

(II)

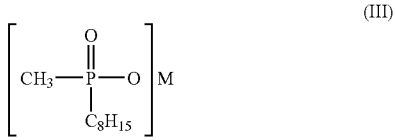

(III)

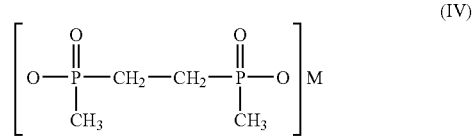

(IV)

European Patent Publication No. 794,191 discloses the use of cyclic aluminum salts of 1-hydroxydihydrophosphole oxide and 1-hydroxyphospholane oxides (see formulae V, VI and VII below) in non-glass filled PBT and nylons. A V-0 rating in PBT was achieved at 20 wt.%

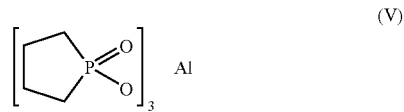

(V)

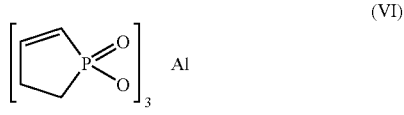

(VI)

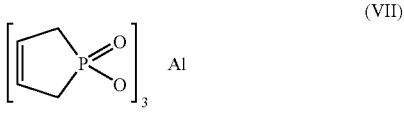

(VII)

The aluminum salts of 1-(methoxyethyl)methylphosphinic (formula VIII below), of (1-ethoxyethyl)methylphosphinic (formula IX below) and of the 1-(methoxyethyl)ethylphosphinic acids (formulae X below) were disclosed in European Patent Publication No. 971,936. These products showed only a V-1 rating at 20 wt. % loading in glass-filled PBT.

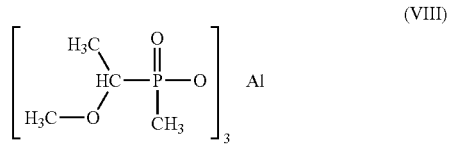

(VIII)

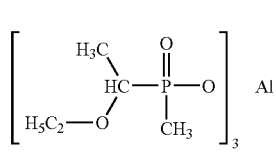 (IX)

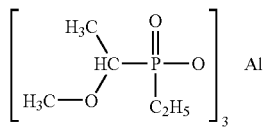 (X)

In spite of a relatively high phosphorus content, the aluminum salt of hydroxymethylmethylphosphinic acid (formula XI below) was less efficient and showed a V-2 rating in glass-filled PBT as exemplified in the U.S. Pat. No. 6,303,674.

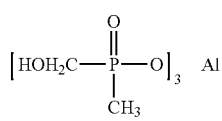 (XI)

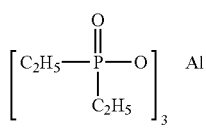 (XII)

Although the aluminum salt of ethylmethylphosphinic acid (formula I above) and the aluminum salt of diethylphosphinic acid (formula XII above) are not particularly effective in nylons, they are synergistic with nitrogen-containing products like melamine cyanurate (see U.S. Pat. Nos. 6,255,371; 6,365,071; and 6,503,969) or melamine phosphate (see U.S. Pat. No. 6,207,736). These combinations are more effective in nylons than are the individual components.

As mentioned above, the mechanism for flame retardant activity for phosphorus-containing flame retardants is usually the condensed phase. Phosphorus containing flame retardants possessing the gas phase characteristic are rare since not only must the flame retardant not react with the decomposing polymer but the phosphorus containing compound must also possess the right degree of volatility so as not to be lost during processing of the polymer compositions in which they are added (i.e., not volatilize at too low a temperature) and not volatilize at too high a temperature, so as to be inefficient during combustion. Phosphorus-containing flame retardant additives possessing these desired properties are therefore highly desirable.

BRIEF SUMMARY OF INVENTION

In accordance with the present invention, it has been surprisingly found that certain phosphorus containing compounds, particularly those metal salts of phosphinic acid of the general formula:

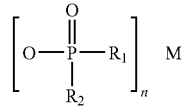

wherein $R_1$ and $R_2$ are the same or different branched $C_3$ to $C_{15}$ alkyl, are highly efficient flame retardant additives. By highly efficient it is meant that these additives possess precisely the right degree of volatility so as to provide high gas-phase activity upon decomposition of the polymer in the course of combustion. By right degree of volatility, it is meant that the additive does not volatilize too early so as to be lost during processing of the polymer nor volatize too late so as to be inefficient during combustion and in general does not react with the polymer prior to volatilization.

DETAILED DESCRIPTION OF THE INVENTION

Figure 1:
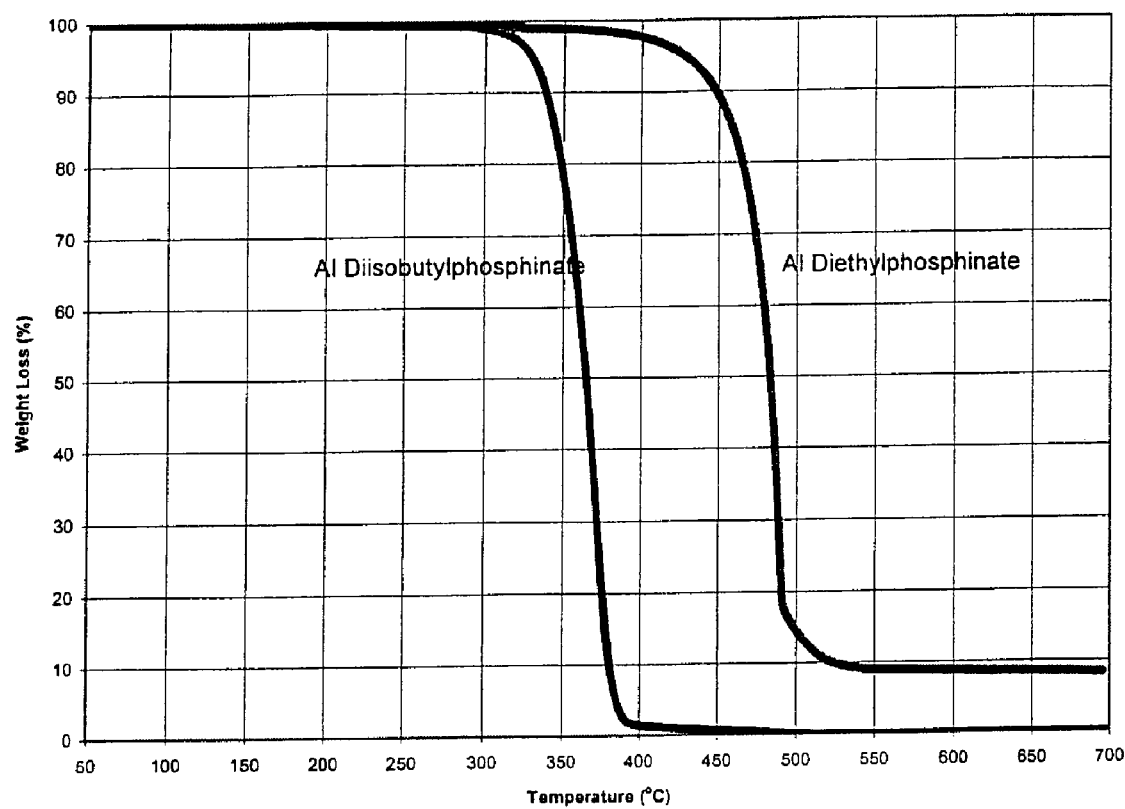
FIG. 1 is a graphical illustration comparing the thermogravimetric analyses of two aluminum salts of phosphinic acid.

The term "thermoplastic polymer", used in this invention is intended to include any organic polymeric material that can be reprocessed and reshaped at the temperature above its softening or melting point. Thermoplastic polymers are usually processed by extrusion and injection molding techniques, but the processing of these materials is not limited to these two techniques. Examples of such thermoplastic polymers are polyethylene, polypropylene, polystyrene, high impact polystyrene (HIPS), acrylonitrile-butadiene-styrene (ABS), polyamide, thermoplastic polyesters, nylons, polycarbonate, polyphenylene ether and their blends.

The term "thermoplastic polyester", as used herein, is intended to include any polymeric thermoplastic material containing ester groups, —O—C(O)—, in the main chain. More particularly, the present invention is related, in a preferred embodiment thereof, to the two most commonly used thermoplastic polyesters: poly(butylene terephthalate) and poly(ethylene terephthalate).

The term "nylon", as used herein, is intended to include any polymeric thermoplastic material containing amide groups, —NH—C(O)—, in the main chain. More particularly, this invention is related, in another preferred embodiment, to the two most commonly used nylons: nylon-6 and nylon-6,6.

In many electronic and electrical applications where flame retardancy is required, thermoplastic polyesters and nylons are filled with inorganic powdered filler, such as silica, talc and the like or reinforcing fibers, such as graphite or chopped glass fiber. In a preferred embodiment, the present invention relates to glass fiber-filled thermoplastic polyesters or nylons.

The phosphorus containing flame retardant additives used in accordance with the present invention are metal salts of phosphinic acid of the general formula:

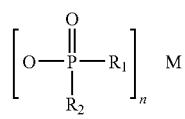

wherein $R_1$ and $R_2$ are same or different branched $C_3$ to $C_{15}$ alkyl, preferably branched $C_4$ to $C_8$ alkyl, for example isobutyl, isopentyl, neopentyl, isohexyl and the like. Most preferably $R_1$ and $R_2$ are isobutyl. The metal (M) is preferably multivalent and is selected from Groups II, III or IV of the Periodic Table or a transition metal. Typical metals include aluminum, magnesium, calcium, strontium, zinc, copper, iron, zirconium and titanium. Aluminum is preferred. The value of n depends on the valence of the metal (M). Typically n is 2 to 4. A most preferred flame retardant additive in accordance with the present invention is aluminum diisobutylphosphinate acid. Upon heating, the metal salt should mostly volatilize in order to provide a gas phase mechanism of action. Preferably, the salt should volatilize substantially completely as measured by thermogravimetry in inert atmosphere at a linear heating rate. In regard to the present invention, this volatilization begins at about 300° C. (at the onset of weight loss, i.e., about 2% weight loss of the salt) and is substantially complete at about 500° C., more preferably about 400° C., when measured at a heating gradient of 10° C./minute in an inert atmosphere.

The phosphorus-containing flame retardant should be present at a level of from about 3% to about 30%, by weight, of the total weight of the composition. Preferred levels are from about 5% to about 20%. The composition can contain one or more other functional additives that are normally employed in such systems including anti-drip agents, dispersants, toughening agents, processing aid additives, charring catalysts and the like.

The present invention is further illustrated by the following representative Examples.

EXAMPLE I

Into a 3 L three-necked flask equipped with condenser, additional funnel, magnetic stirrer and thermometer were charged 318.03 g (3.00 moles) of sodium hypophosphite monohydrate and 637 g of acetic acid. The mixture was heated to 70° C. and gradually became a clear solution. Then, 149.33 g of 95-98% sulfuric acid was slowly added into the mixture and substantial precipitation was observed. To this mixture was then added a solution of 436.4 g (5.897 moles) of tert-butyl alcohol, 120 g of acetic acid and 22.5 g (0.15 mole) of tert-butyl peroxide at temperature of 115° C. to 100° C. over the course of seventeen hours. After addition was done, $^{31}$P NMR showed that the mixture contained 73% of diisobutylphosphinic acid, 25% of isobutylphosphinic acid, 1% of phosphonate acid and 1% of phosphate acid. The mixture was dried in a rotary evaporator under vacuum at 95° C. to remove water and solvent, and was then washed three times with a 2.7% sodium carbonate aqueous solution. The top oily phase was separated and was dried in a rotary evaporator under vacuum at 95° C. Oily materials (330 g) were then collected and were crystallized at room temperature. The total yield was 62% without recycling of the mother liquid. Then, 136 g (0.764 mole) of diisobutylphosphinic acid was dissolved in a mixed solvent of water and acetonitrile and was neutralized by dilute aqueous sodium hydroxide solution. To 61.83 g (0.256 mole) of an aqueous aluminum chloride hexahydrate solution was gradually added neutralized diisobutylphosphinic acid. A substantial amount of white precipitants was observed. The precipitants were then filtered, were washed with 3×50 mL of acetonitrile and with 5×400 mL water and were then dried overnight in an oven at 105° C. A white solid (136 g), identified as the aluminum salt of diisobutylphosphinic acid (ABPA), was obtained at a yield of 96%.

EXAMPLE 2

Thermogravimetric analysis was run on about 10 mg of the sample from Example 1 in an inert flow of nitrogen at a linear heating rate of 10° C./min. FIG. 1 shows that this aluminum salt of diisobutylphosphinic acid (ABPA) completely volatilized within the temperature range of 300° C. to 400° C. On the other hand, the aluminum salt of diethylphosphinic acid volatilized in the temperature range of 400° C. to 500° C. and left about 10% of solid residues, indicating that this salt did not volatilize completely, but was partially decomposed and yielded a solid residue.

EXAMPLE 3

The aluminum salt of diisobutylphosphinic acid (ABPA) prepared in Example 1 was formulated with a glass-fiber filled PBT (VALOX 420 brand from General Electric) by extrusion of the resin using a twin-screw extruder. ABPA (125 g) was blended with 875 g of PBT before extrusion, and this blended composition was then fed into the extruder. The extruded resin formulation was quenched in water and was pelletized. Standard specimens for combustion test of ⅛ and 1/16-inch thicknesses were prepared by injection molding of the thoroughly dried formulation. The fire retardant test was performed according to the UL-94 protocol (vertical setup), which is described by J. Troitzsch, Plastics Flammability Handbook, 3$^{rd}$ edition, Hanser Publishers, Munich, 2004. The ⅛ inch specimens gave a V-0 rating and the 1/16 inch specimens gave a V-2 rating.

EXAMPLE 4

The ABPA prepared in Example 1 (3 g) was formulated with 57 g of glass fiber-filled nylon (ZYTEL 73G33 brand from DuPont) by melt blending in a bowl mixer at 230° C. The compounded plastic was then compressed into a slab of ⅛ inch thickness, and then standard specimens for combustion test were cut out of the slab. The specimens showed a V-0 rating in the UL-94 test.

EXAMPLE 5

The ABPA prepared in Example 1 (100 g) was formulated with 900 g of glass fiber-filled nylon (ZYTEL 73G33 brand from DuPont) as described in Example 3. The specimens of ⅛ and 1/16 inch thickness both showed a V-0 rating in the UL-94 test.

COMPARATIVE EXAMPLE 6

The aluminum salt of diethylphosphinic acid, 100 g, was formulated with 900 g of glass fiber-filled nylon (ZYTEL 73G33 brand from DuPont) as described in Example 3. Specimens of ⅛ inch thickness showed a V-1 rating in the UL-94 test, whereas specimens of 1/16 thickness failed this test.

The foregoing examples illustrate certain embodiments of the present invention and for that reason should not be construed in a limiting sense. The scope of protection that is sought is set forth in the claims that follow.

What is claimed is:

1. A flame retardant thermoplastic nylon composition comprising a thermoplastic nylon polymer and an effective flame retardant amount of an aluminum salt of diisobutylphosphinic acid, wherein said aluminum salt begins to volatilize at about 300° C. as measured by thermogravimetric analysis at a linear heating rate of 10° C./minute in an inert atmosphere.

2. The composition of claim 1 wherein the nylon is glass-filled nylon.

3. The composition of claim 1 wherein the aluminum salt begins to volatilize at about 300° C., and substantially ceases volatilization at about 500° C.

4. The composition of claim 1, wherein, the aluminum salt begins to volatilize at about 300° C., and substantially ceases volatilization at about 400° C.

5. The composition of claim 1 wherein said aluminum salt of diisobutylphosphinic acid is present in an amount of from about 3 to about 30 percent by weight of the total composition.

6. The composition of claim 1 wherein said aluminum salt of diisobutylphosphinic acid is present in an amount of from about 3 to about 30 percent by weight of the total composition.

7. The composition of claim 5 wherein the aluminum salt of diisobutylphosphinic acid is present in an amount of from about 5 to about 20 percent by weight of the total composition.

8. The composition of claim 6 wherein the aluminum salt of diisobutylphosphinic acid is present in an amount of from about 5 to about 20 percent by weight of the total composition.

9. A flame retardant thermoplastic nylon composition comprising a thermoplastic nylon polymer and an effective flame retardant amount of aluminum diisobutylphosphinate.

10. A flame retardant thermoplastic nylon composition consisting essentially of a thermoplastic nylon polymer and an effective flame retardant amount of an aluminum salt of diisobutylphosphinic acid, wherein said aluminum salt begins to volatilize at about 300° C. as measured by thermogravimetric analysis at a linear heating rate of 10° C./minute in an inert atmosphere.

11. The composition of claim 10 wherein the thermoplastic nylon is glass-filled.

12. The composition of claim 10 wherein the aluminum salt begins to volatilize at about 300° C., and substantially ceases volatilization at about 500° C.

13. The composition of claim 10, wherein, the aluminum salt begins to volatilize at about 300° C., and substantially ceases volatilization at about 400° C.

* * * * *